(12) United States Patent
Golden et al.

(10) Patent No.: US 8,876,704 B2
(45) Date of Patent: Nov. 4, 2014

(54) MEDICAL DEVICE

(75) Inventors: John Golden, Norton, MA (US); Sean McWeeney, Brighton, MA (US); Robert Castoldi, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1350 days.

(21) Appl. No.: 12/353,894

(22) Filed: Jan. 14, 2009

(65) Prior Publication Data

US 2009/0182200 A1      Jul. 16, 2009

Related U.S. Application Data

(60) Provisional application No. 61/021,003, filed on Jan. 14, 2008.

(51) Int. Cl.
| | | |
|---|---|---|
| *A61B 1/00* | (2006.01) | |
| *A61M 25/01* | (2006.01) | |
| *A61M 25/00* | (2006.01) | |
| *A61B 1/04* | (2006.01) | |

(52) U.S. Cl.
CPC ... *A61M 25/0147* (2013.01); *A61M 2025/0183* (2013.01); *A61M 25/0043* (2013.01)
USPC .......................................... 600/153; 600/114

(58) Field of Classification Search
CPC ........... A61B 1/00075; A61B 1/00087; A61B 1/00135; A61B 1/00147; A61B 1/00154
USPC .......... 600/153, 139, 114, 121–125, 156–158
See application file for complete search history.

(56) References Cited

U.S. PATENT DOCUMENTS

| | | | |
|---|---|---|---|
| 3,874,388 A | | 4/1975 | King et al. |
| 4,690,175 A | * | 9/1987 | Ouchi et al. .................. 138/131 |
| 4,869,238 A | * | 9/1989 | Opie et al. .................... 600/109 |
| 4,921,326 A | * | 5/1990 | Wild et al. .................... 385/117 |
| 5,024,234 A | * | 6/1991 | Leary et al. .................. 600/467 |
| 5,180,368 A | | 1/1993 | Garrison |

(Continued)

FOREIGN PATENT DOCUMENTS

| | | |
|---|---|---|
| EP | 0904795 A1 | 3/1991 |
| EP | 1 454 587 A2 | 9/2004 |

(Continued)

OTHER PUBLICATIONS

International Search Report mailed Jun. 5, 2009, issued in corresponding International Application No. PCT/US2009/031014, filed Jan. 14, 2009.

(Continued)

*Primary Examiner* — Alireza Nia
(74) *Attorney, Agent, or Firm* — Bookoff McAndrews, PLLC

(57) ABSTRACT

Apparatuses of the type broadly applicable to numerous medical applications in which it is desirable to insert one or more steerable or non-steerable catheters or similar devices into a working channel of an associated device, such as an endoscope, catheter, etc., or passageway of a patient, are disclosed. The apparatuses may include catheters having a dedicated guide wire channel and one or more of the following: viewing capabilities, a working channel, and auxiliary channels, such as insufflation/irrigation channels. The catheters may include a guide wire channel that is configured to provide the catheter or other device with rapid exchange capabilities.

25 Claims, 12 Drawing Sheets

(56) References Cited

U.S. PATENT DOCUMENTS

| | | | |
|---|---|---|---|
| 5,395,335 A | 3/1995 | Jang | |
| 5,456,680 A | 10/1995 | Taylor | |
| 5,860,923 A * | 1/1999 | Lenker et al. | 600/433 |
| 6,606,515 B1 * | 8/2003 | Windheuser et al. | 600/434 |
| 6,869,416 B2 * | 3/2005 | Windheuser et al. | 604/164.05 |
| 7,172,577 B2 | 2/2007 | Mangano et al. | |
| 7,264,001 B2 | 9/2007 | Boutillette et al. | |
| 7,922,650 B2 | 4/2011 | McWeeney et al. | |
| 7,922,654 B2 | 4/2011 | Boutillette et al. | |
| 2003/0109861 A1 * | 6/2003 | Shimada | 606/14 |
| 2004/0034311 A1 | 2/2004 | Mihalcik | |
| 2004/0102719 A1 | 5/2004 | Keith | |
| 2006/0252993 A1 * | 11/2006 | Freed et al. | 600/146 |

FOREIGN PATENT DOCUMENTS

| | | | |
|---|---|---|---|
| EP | 1532998 A2 | 5/2005 | |
| EP | 1 595 504 A1 | 11/2005 | |
| JP | 2002-543937 | 12/2002 | |
| JP | 2007-530155 | 11/2007 | |
| WO | 93/18818 A1 | 9/1993 | |
| WO | 00/69499 A1 | 11/2000 | |
| WO | WO 01/21246 A1 | 3/2001 | |
| WO | 0149356 A1 | 7/2001 | |
| WO | 0189624 A1 | 11/2001 | |
| WO | 02/96483 A2 | 5/2002 | |
| WO | 03047447 A1 | 6/2003 | |
| WO | 03101287 A2 | 12/2003 | |
| WO | WO 2005/094665 A2 | 10/2005 | |
| WO | WO 2006/020374 A2 | 2/2006 | |
| WO | 2008/033589 A1 | 3/2008 | |

OTHER PUBLICATIONS

Partial International Search Report mailed on Apr. 7, 2009, issued in corresponding International Application No. PCT/US2009/031014, filed Jan. 14, 2009.

* cited by examiner

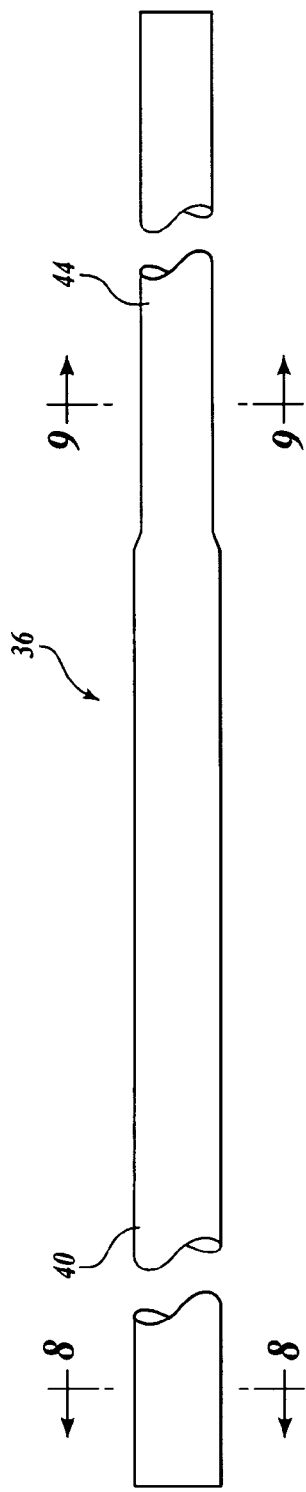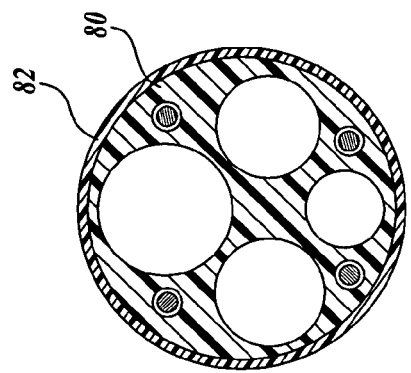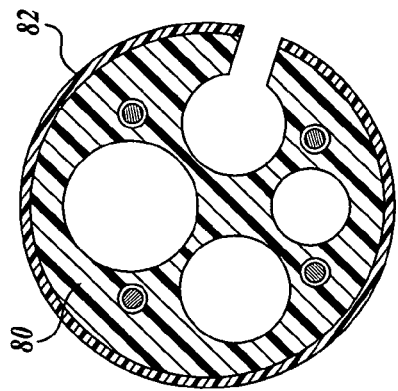

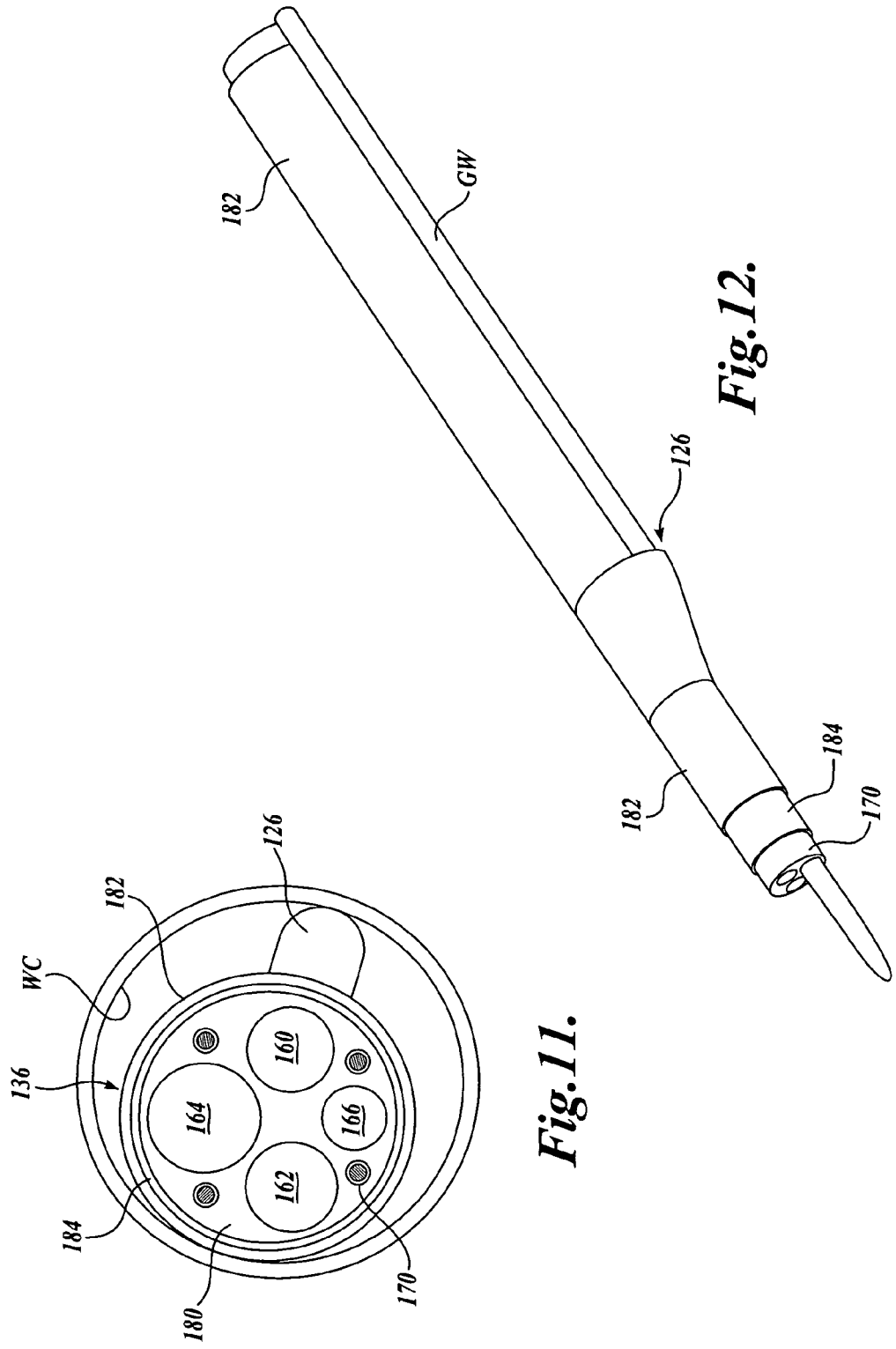

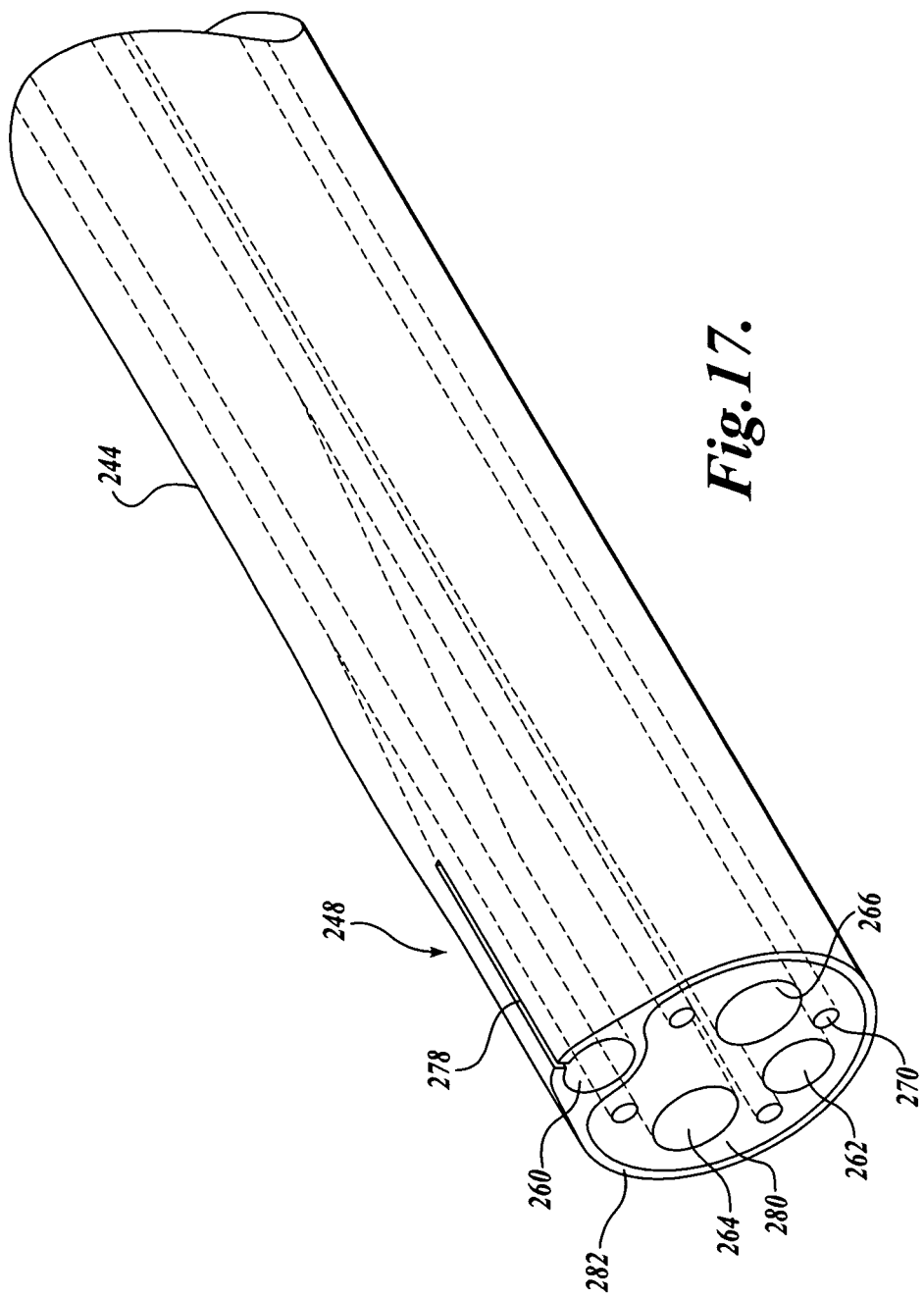

MEDICAL DEVICE

CROSS-REFERENCE TO RELATED APPLICATION

This application claims the benefit of U.S. Provisional Application No. 61/021,003, filed Jan. 14, 2008, the disclosure of which is hereby incorporated by reference.

BACKGROUND

A challenge in the exploration and treatment of internal areas of the human anatomy has been adequately visualizing the area of concern. Visualization can be especially troublesome in minimally invasive procedures in which small diameter, elongate instruments, such as catheters and endoscopes, are navigated through natural passageways of a patient to an area of concern either in the passageway or in an organ reachable through the passageway.

Detailed information regarding the anatomy can be discerned from direct viewing of the anatomy provided through one or more of the elongate instruments used in the procedure. Various types of endoscopes configured for use in various passageways of the body such as the esophagus, rectum or bronchus can be equipped with direct viewing capability through the use of optical fibers extending through the length of the scope, or with digital sensors, such as CCD or CMOS. However, because endoscopes also provide a working channel through which other medical instruments must pass, optional lighting bundles and components to provide steering capability at its distal end, the scope is typically of a relatively large diameter, e.g., 5 mm or greater. This large diameter limits the use of the endoscope to relatively large body channels and prohibits their use in smaller ducts and organs that branch from a large body channel, such as the biliary tree.

Typically, when examining small passageway such as the bile duct or pancreatic duct, the endoscope is used to get close to a smaller passageway or region of concern and another instrument, such as a catheter, is then extended through the working channel of the endoscope and into the smaller passageway. The catheter can be routed over a guide wire pre-placed in the area of interest. Alternatively, a catheter of the steerable type may be steered into the smaller passageway with the aid of images provided from the endoscope, or if the steerable catheter has its own vision capabilities, steered into the smaller passageway with the aid of images provided by the catheter. One such steerable catheter with vision capabilities is described in co-pending U.S. application Ser. No. 11/089,520, filed Mar. 23, 2005, which is hereby incorporated by reference. Once the catheter is in the small passage areas, visualization may be provided via contrast media and/or the vision capabilities of the catheter.

Visualization may reveal selected areas within the area of interest, such as the common bile duct, that require treatment. To treat the selected areas, a different catheter is sometimes required, necessitating a catheter exchange. A catheter exchange typically involves removing the first catheter from the endoscope over a guide wire pre-placed in the area of interest, and advancing a second catheter over the guide wire to the desired treatment site. In order to maintain a handle on the proximal end of the guide wire, it is necessary that the portion of the guide wire that remains outside the patient be longer than the length of the catheter. Therefore, a catheter/guide wire system suitable for these procedures has required the use of long guide wires that can be cumbersome to manipulate and can clutter an operating room.

To address the issues associated with changing catheters over long guide wires, many non-steerable catheters include so-called "rapid exchange" lumens or channels. These rapid exchange catheters typically include an opening on the sheath of a catheter and a slot that extends along the length of the catheter through which a guide wire can be pulled. To exchange the catheter for another device while maintaining the position of the guide wire in the body, the catheter is stripped off the guide wire by pulling it through the slot. A new catheter or device can then be routed over the guide wire by inserting the proximal end of the guide wire into an opening of a guide wire lumen at the distal end of the new device and advanced such that the proximal end of the guide wire exits the opening. The opening may be positioned towards the proximal end of the catheter or may be located more towards the distal end.

While rapid exchange guide wire lumens have been developed for many procedures, they have not been adapted for use with steerable catheters, catheters with vision capabilities, catheters to be routed through the working channels of endoscopes, or catheters that are required to transmit torque from the proximal to the distal end of the catheter.

In addition to performing a catheter exchange procedure, it may also be desirable to perform a guide wire exchange procedure. This may be desirable when, for example, a first guide wire is too large to fit through a desired body duct, or otherwise lacks the desired characteristics. Under these circumstances, a physician may leave the catheter in place, withdraw the first guide wire from the catheter, and insert a second guide wire through the catheter to the desired site. During this procedure, the catheter guides the guide wire to the desired site. Thus, once the catheter is positioned at a target site, it is highly desirable to maintain the position of the catheter during a guide wire exchange procedure so that the second guide wire may be guided directly to the desired site in a minimum amount of time.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with aspects of the present invention, a catheter is provided which comprises an elongated shaft having a proximal end and a distal end, a guide wire channel extending along at least a portion of the shaft in-between the proximal and distal ends, at least one channel disposed within the shaft and extending to the distal end, and a guide wire opening disposed in communication with the guide wire channel of the shaft such that a guide wire may be insertable into the guide wire opening and routed into the guide wire channel. The shaft may be configured for providing radial access from a position exteriorly of the shaft to a portion of the guide wire channel that extends between the guide wire opening and a position proximal the distal end of the shaft in order to allow a guide wire to radially exit the shaft.

In accordance with another aspect of the present invention, a catheter is provided which comprises an elongated shaft having a proximal section and a distal section, a channel for accessing the distal end of the shaft, a guide wire channel extending along at least a portion of the shaft to the distal end of the shaft, and a guide wire port disposed at or near the transition between the proximal section and the distal section of the shaft. The guide wire port defines a guide wire port opening and a guide wire port conduit that communicate with the guide wire channel of the shaft such that a guide wire may be insertable into the guide wire port opening and routed into the guide wire channel. The catheter further comprises a deflector associated with the guide wire port and positionable in the guide wire conduit or the guide wire channel.

In accordance with another aspect of the present invention, a catheter is provided which comprises an elongated shaft having a proximal end and a distal end, a guide wire channel extending along at least a portion of the shaft in-between the proximal and distal ends, at least one optical channel disposed within the shaft and extending to the distal end, a guide wire opening disposed in communication with the guide wire channel of the shaft such that a guide wire may be insertable into the guide wire opening and routed into the guide wire channel, and means disposed along a portion of the shaft for allowing a guide wire to radially exit the shaft.

In accordance with another aspect of the present invention, a catheter is provided which comprises an elongated shaft having a proximal end and a distal end, wherein the elongated shaft comprises an core body an outer sleeve, and an inner reinforcement sheath disposed between the core body and the outer sleeve. The catheter further includes a guide wire channel extending along at least a portion of the shaft in-between the proximal and distal end, a guide wire opening disposed in communication with the guide wire channel of the shaft such that a guide wire may be insertable into the guide wire opening and routed into the guide wire channel, and means disposed along a section of the shaft for allowing a guide wire to radially exit the shaft, wherein the means is disposed outwardly of the inner reinforcement sheath for at least a first portion of the section of the shaft and disposed inwardly of the inner reinforcement sheath for at least a second portion of the section of the shaft.

In accordance with another aspect of the present invention, a catheter is provided which comprises an elongated shaft having a proximal end and a distal end. The shaft has a proximal section having a first diameter and a distal section having a second, smaller diameter. The catheter further includes a guide wire channel extending along a portion of the shaft in-between the proximal and distal end, at least two channels selected from the group consisting of a working channel, an optical channel, and a fluid channel, disposed within the shaft and extending to the distal end, and a guide wire opening disposed in communication with the guide wire channel of the shaft such that a guide wire may be insertable into the guide wire opening and routed into the guide wire channel, wherein the shaft includes a rapid exchange channel section along a portion thereof.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 7 is a plan view of an exemplary embodiment of a catheter formed in accordance with aspects of the present invention;

FIG. 8 is a cross-sectional view taken along line 8-8 in FIG. 7;

FIG. 9 is a cross-sectional view taken along line 9-9 in FIG. 7;

FIG. 11 is an end view of a catheter of the catheter assembly shown in FIG. 10, wherein a catheter of the catheter assembly is inserted into a working channel of an endoscope;

FIG. 12 is a partial perspective view of the catheter shown in FIGS. 10 and 11;

FIG. 17 is a partial perspective view of a taper or transition section formed in accordance with aspects of the present invention;

DETAILED DESCRIPTION

Embodiments of the present invention will now be described with reference to the drawings where like numerals correspond to like elements. Embodiments of the present invention are directed to apparatuses of the type broadly applicable to numerous medical applications in which it is desirable to insert one or more steerable or non-steerable catheters or similar devices into a working channel of an associated device, such as an endoscope, catheter, etc., or passageway of a patient. Embodiments of the present invention are generally directed to features and aspects of a catheter having a dedicated guide wire channel and one or more of the following: viewing capabilities, a working channel, and auxiliary channels, such as insufflation/irrigation channels. In embodiments of the present invention, the guide wire channel may be configured to provide the catheter or other device with rapid exchange capabilities.

As will be described in detail below, the catheter may obtain viewing capabilities for viewing anatomical structures within the body by being constructed as a vision catheter or by having a fiberscope or other viewing device selectively routed through one of its channels. As such, embodiments of the present invention can be used for a variety of different diagnostic and interventional procedures. The catheter may be of the steerable type so that the distal end of the catheter may be steered from its proximal end as it is advanced within the body or of the non-steerable type. A suitable use for the catheters described herein includes, but is not limited to, diagnosis and/or treatment of the duodenum, and particularly the biliary tree.

Although exemplary embodiments of the present invention may be described hereinafter as suitable for use with duodenoscopes, it will be appreciated that embodiments of the present invention and aspects thereof have wide application, and may be suitable for use with other endoscopes (e.g., ureteroscopes) or medical devices, such as catheters (e.g., guide catheters, electrode catheters, angioplasty catheters, etc.). Accordingly, the following descriptions and illustrations herein should be considered illustrative in nature, and thus, not limiting the scope of the present invention. Additionally, embodiments of the catheter may be utilized alone, as well as in conjunction with a conventional endoscope.

Figure 1:
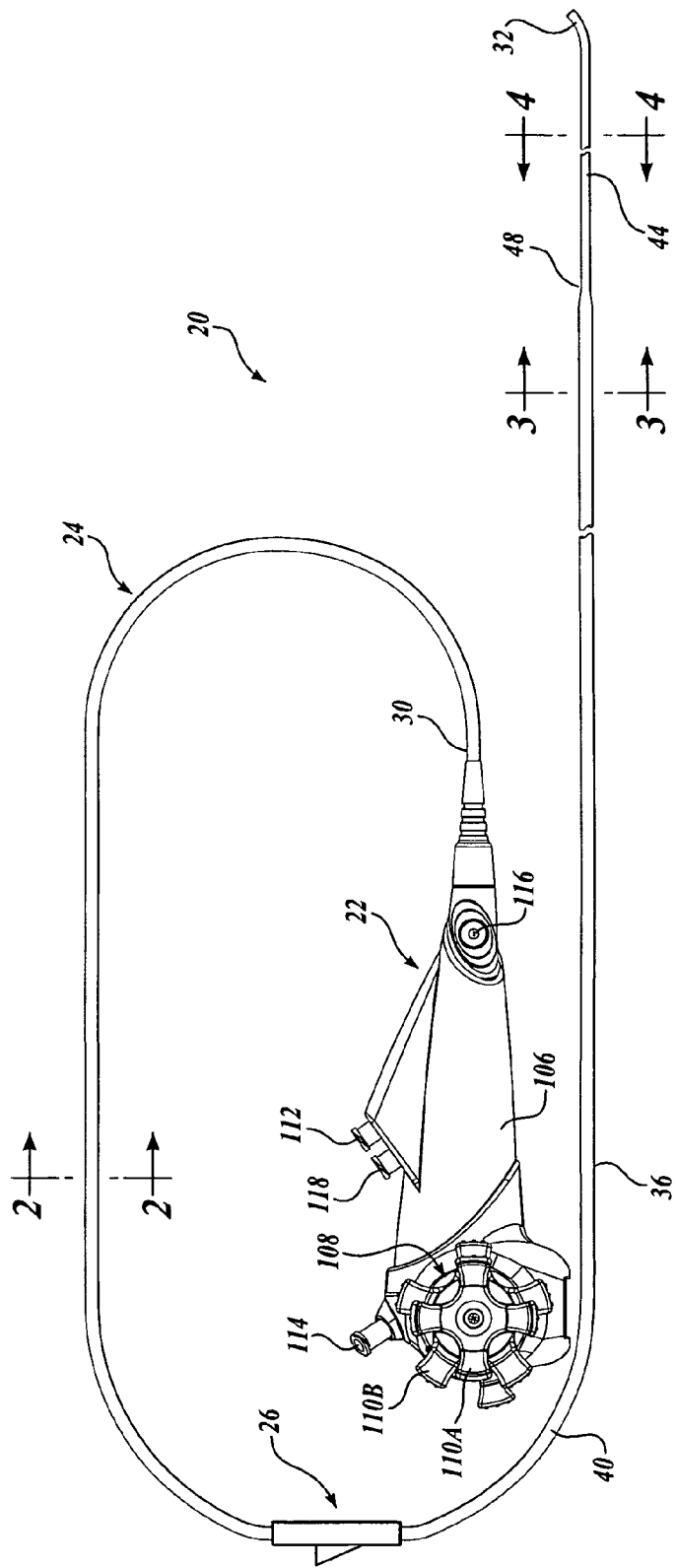
FIG. 1 is a plan view of an exemplary embodiment of a catheter assembly formed in accordance with aspects of the present invention.

Referring now to FIG. 1, there is shown a representative embodiment of a catheter assembly, generally designated 20, formed in accordance with aspects of the present invention. In the embodiment of FIG. 1, the catheter assembly 20 includes a catheter handle 22, a catheter 24, and an optional guide wire port 26 positioned along a portion of the catheter 24. The catheter 24 includes a proximal end 30 that may be operatively connected to the catheter handle 22 and a distal end 32 that may be inserted into, for example, a working channel of an endoscope, such as a duodenoscope, or a passageway of a patient. The catheter 24 as shown includes a shaft 36 comprising a proximal section 40, a distal section 44, and an optional taper 48, which acts as a transition between the proximal section 40 and the distal section 44 of the catheter 24.

In the embodiment shown, the proximal section 40 has a larger cross-sectional area, e.g., diameter, than the distal section 44, although in other embodiments, the proximal section 40 and the distal section 44 may have the same generally uniform cross-sectional area. As such, the taper 48 may be omitted in these latter embodiments. The catheter 24 may further be of the steerable or deflectable type, and thus, the distal section 44 may either include an articulating section or may be constructed of a more flexible material than the proximal section 40 for aiding in the deflection of the distal end 32.

Figure 2:
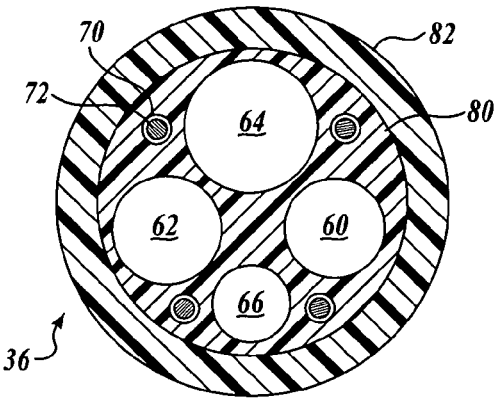
FIG. 2 is a cross-sectional view taken along line 2-2 in FIG. 1.
Figure 3:
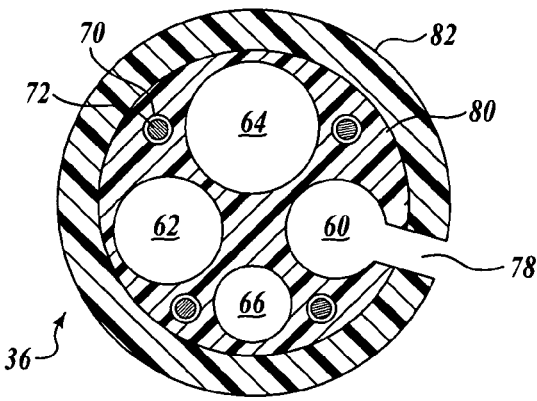
FIG. 3 is a cross-sectional view taken along line 3-3 in FIG. 1.
Figure 4:
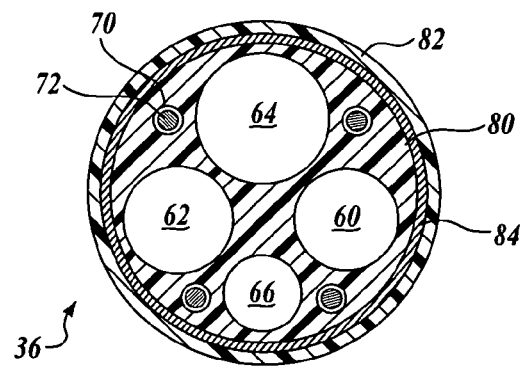
FIG. 4 is a cross-sectional view taken along line 4-4 in FIG. 1.

Referring now to FIGS. 2-4, one exemplary embodiment of the catheter shaft 36 is shown in more detail. FIGS. 2-4 are cross-sectional views of the proximal section 40 taken proximally and distally of the guide wire port 26 and of the distal section 44, respectively. As best shown in FIGS. 2-4, the catheter shaft 36 includes a dedicated guide wire channel 60 and one or more channels 62, 64, and 66 for providing access to a treatment area located at the distal end of the catheter.

In the embodiment shown in FIGS. 2-4, the dedicated guide wire channel 60 extends the entire length of the catheter through which a guide wire can be routed to and from the treatment area. In other embodiments, the guide wire channel 60 may not extend the entire length of the catheter shaft but instead extends only a portion thereof, for example, from one of many positions located distally of the proximal end to the catheter distal end. As will be described in more detail below, a portion of the catheter shaft is slitted, slotted or otherwise configured to provide access along the catheter shaft 36 for providing rapid exchange capabilities to the catheter.

The one or more channels 62, 64, and 66 may extend from a position proximal of the distal end of the catheter shaft 36. For example, the one or more channels 62, 64, and 66 may extend to the distal end of the catheter shaft 36 from either the proximal end of the catheter or a position proximal of the catheter distal end.

As best shown in FIGS. 2-4, the one or more channels may include an optical channel 62. The optical channel 62 allows for the passage of a fiberscope, optical fiber cable, optical assembly, or other small diameter viewing catheter or device to the distal end of the catheter. In other embodiments, a fiberscope, optical fiber cable or the like may be permanently secured in place within the channel. Alternatively, the catheter 24 may be constructed as a video catheter, and as such, viewing capabilities are provided by an image sensor, such as a CCD, CMOS, or photo diode, mounted at or adjacent the distal end of the catheter 24. In this embodiment, the catheter may include other components, such as illumination sources, e.g., LEDs, etc., and associated power and signal transmission cabling, etc. It will be appreciated that in this embodiment, the optical channel may be used to provide a source of illumination to the distal tip by routing an illumination fiber therethrough, or such optical channel may be omitted.

The one or more channels may also include a working channel 64. The working channel 60 allows for the passage of various treatment or diagnostic devices, such as stone retrieval baskets, lasers, biopsy forceps, etc. to and from the treatment area located distally of the catheter distal end. The one or more channels may further include an additional channel 66 for use as an irrigation/insufflation channel, a fluid delivery channel, or multi-purpose channel. The channel 66 allows the passage of liquids, gases, and/or device to and from the treatment area.

As was described briefly above, in several embodiments of the present invention, the catheter 24 may be of a steerable-type, and thus, the catheter shaft 36 may optionally include one or more steering wire channels 70 that extend substantially the length of the catheter 24 for deflecting the distal end of the catheter shaft 36 in one or more directions. In the embodiment shown in FIGS. 2-4, steering wires 72 can be routed through a corresponding number of steering wire channels 70, extend from the distal end of the catheter to the opposing, proximal end of the catheter, and terminate in a suitable manner with a steering mechanism associated with the catheter handle 22, as will be described in detail below. The steering wires 72 may be attached at anchor points to the distal section near or at the distal end of the catheter via conventional techniques, such as adhesive bonding, heat bonding, crimping, laser welding, resistance welding, soldering, etc., such that movement of the wires causes the distal end to deflect in a controllable manner. In one embodiment, the steering wires 72 are attached via welding or adhesive bonding to a fluoroscopy marker band (not shown) fixedly attached to the distal section. In this embodiment, the band may be held in place via adhesive and/or an outer sleeve.

The steering wires 72 preferably have sufficient tensile strength and modulus of elasticity that they do not deform (elongate) during curved deflection. In one embodiment, the steering wires are made from 304 stainless steel with an 0.008 inch diameter and have a tensile strength of approximately 325 KPSI. The steering wires 72 can optionally be housed in a PTFE thin-walled extrusion (not shown) to aid in lubricity and prevent the catheter 24 from binding up during deflections, if desired. For a more detailed description of types of steering wires and catheter shaft configurations that may be practiced with the present invention, please see co-pending U.S. application Ser. No. 11/089,520, which is hereby incorporated by reference.

In the illustrated embodiment shown in FIGS. 2-4, the catheter 24 includes two pairs of steering wires 72 that controllably steer the catheter 24 in two substantially perpendicular planes. In alternative embodiments, the catheter 24 includes one pair of steering wires 72 that allow the user to steer the distal end in one plane. In a further embodiment, the catheter 24 only includes one steering wire 72 that allows the user to steer the distal end in one direction. In another embodiment, the steering wires may be omitted, and thus, the catheter 24 can be of a non-steerable type. In such an embodiment, the catheter can be advanced over a guide wire (not shown) pre-placed, for example, in the bile or pancreatic duct (referred in the art as "back loading" the catheter).

The dedicated guide wire channel 60, the one or more channels 62, 64, and 66, and the optional steering channels 70 may be separate tubular members, which are routed through a tubular catheter shaft. Alternatively, in the embodiment shown in FIGS. 2-4, the catheter shaft 36 may comprise a core body 80 that defines the dedicated guide wire channel 60, the one or more channels 62, 64, and 66, and the optional steering wire channels 70. In this embodiment, the core body 80 of the catheter shaft 36 may be constructed from any suitable material, such as Pebax® (polyether block amides), nylon, polytetrafluoroethylene (PTFE), polyethylene, polyurethane, fluorinated ethylene propylene (FEP), thermoplastic elastomers and the like, or combinations or blends thereof. The core body 80 of the catheter shaft 36 may be formed as a one-piece design using known techniques in the art, such as extrusion, or may be formed in multiple segments, for example, multiple extruded sections, using one or more materials, which are then subsequently joined by heat bonding, adhesive bonding, lamination or other known techniques.

The embodiment of the catheter shaft 36 shown in FIGS. 2-4 may optionally include an outer sleeve 82. The outer sleeve 82 may extend the length of the catheter or sections thereof. The outer sleeve 82 may comprise one of any number of polymer jackets that are laminated, co-extruded, heat shrunk, adhesive bonded, or otherwise attached over the core body 80. Suitable materials for the sleeve 82 include, but are not limited to, polyethylene, nylon, Pebax® (polyether block amides), polyurethane, polytetrafluoroethylene (PTFE), and thermoplastic elastomers to name a few. The outer sleeve 82 may be used to vary the stiffness of the catheter, if desired, or to provide improved torque transfer and/or other desirable catheter properties. Additionally, the sleeve 82 may be used as one convenient method for securing a more flexible distal section 44 to the proximal section 40.

In several embodiments, the external surface of the sleeve 82 may have a hydrophilic coating or a silicon coating to ease the passage of the device in-vivo. Such a hydrophilic coating can be, for example, but not limited to, N-Vinyl Pyrrolidone, Poly Vinyl Alcohol, and Poly Vinyl Pyrrolidone. The hydrophilic coating can be accomplished by coating the device with a primer, such as Bayhydrol 110 (an anionic dispersion of an aliphatic polyester urethane resin in water/n-methyl-2pyrrolidone) and then bonding the primary layer over the primer. The primary layer can be, for example, but not limited to, an acrylamide or a polyurethane-based acrylamide. Alliphatic polyether and polyester polyurethanes also can be used as lubricous coatings.

In the embodiment shown in FIGS. 2-4, the outer sleeve 82 disposed on the proximal section 40 is thicker than the outer sleeve 82 disposed on the distal section for increasing the stiffness and torsional rigidity of the proximal section 40 of the catheter shaft 36. In another embodiment shown in FIGS. 7-9, the diameter of the core body 80 of the proximal section 40 is greater than the diameter of the core body 80 of the distal section 44 while the outer sleeve 82 is somewhat uniform in thickness as it extends from the beginning of the proximal section 40 to the end of the distal section 44. In this embodiment, the larger core body of the proximal section increases the stiffness and/or torsional rigidity of the shaft.

In other embodiments, the catheter 24 may optionally include an inner reinforcement sheath 84 disposed between the core body 80 and the outer sleeve 82 along the distal section 44 (see FIG. 1) of the catheter shaft 36 as shown in cross-section in FIG. 4. The sheath 84 may be a woven or layered structure, such as a braided design of fine wire or polymeric elements (0.001 inches to 0.010 inches in diameter) woven or coiled together along the longitudinal axis of the catheter with conventional catheter braiding techniques. This allows the distal section of the catheter to be advanced to the desired anatomical site by increasing the column strength of the distal section while also increasing its torsional rigidity. Conventional coiled polymer or braid wire may also be used for this component with coil wire dimensioning ranging in width from 0.002 to 0.120 inches and thicknesses from 0.002 to 0.10 inches. Braided ribbon wire may also be used for the sheath. In one embodiment, the outer sleeve 82 is coextruded, coated, or otherwise attached, once the reinforcement layer 84 is applied to the distal section, to lock the reinforcement layer in place and secure it to the distal section core body 80. In one embodiment, the portion of the proximal section that extends from the proximal end to the beginning of the guide wire opening may also include a reinforcement sheath.

Figure 6:
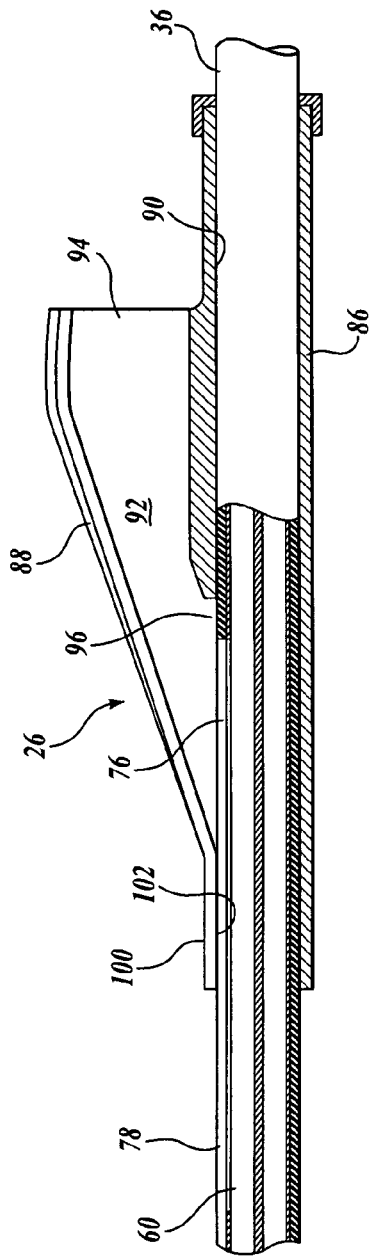
FIG. 6 is a cross-sectional view of the guide wire port of FIG. 5.
Figure 5:
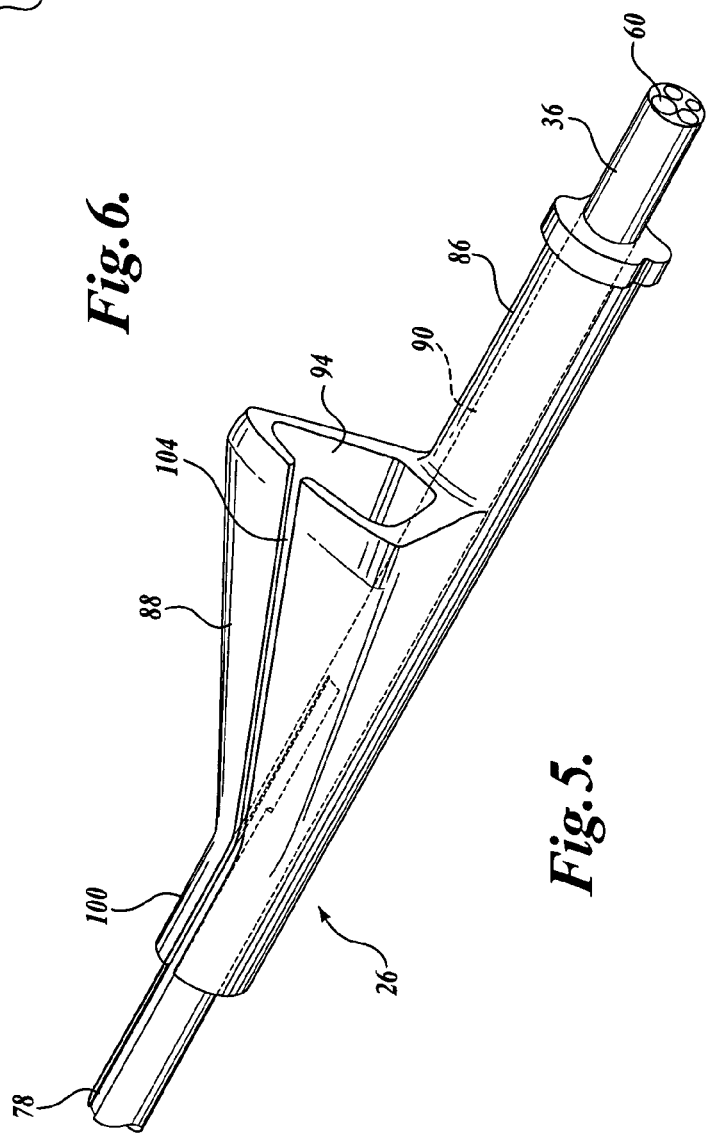
FIG. 5 is a perspective view of one exemplary embodiment of a guide wire port formed in accordance with aspects of the present invention.

Turning now to FIGS. 5 and 6, the catheter shaft 36 may also include an opening 76 formed along a portion of the outer surface of the shaft 36 and positioned proximal the distal section 44. The opening 76 is formed so as to communicate with the guide wire channel 60 from a position external the shaft. Referring to FIG. 1, the shaft opening (hidden by the guide wire port 26) may be positioned proximate or near the proximal end 30 of the catheter 24 or may be disposed further distally of the proximal end 30 along the catheter 24 toward the optional taper 48. Although it should be recognized that the shaft opening may be located at any location distally of the proximal end 30 of the catheter 24, in one embodiment the shaft opening is located approximately between 140 and 180 centimeters (cm) from the taper 48 and/or the beginning of the distal section 44. In this manner, the catheter 24 may be utilized with a 260 cm or similar guide wire, as will be described in detail below. As will be described in detail below, the shaft opening 76 (FIGS. 5 and 6) in one embodiment communicates with the guide wire port 26 for facilitating the insertion of a guide wire into the guide wire channel during use.

Returning to FIGS. 5 and 6, the catheter shaft 36 may further include a slit, a slot, or other means for allowing a guide wire to radially exit the guide wire channel 60 along a portion of the shaft 36, thereby providing rapid exchange capabilities to the catheter. In the illustrated embodiment of FIGS. 5 and 6, the catheter shaft 36 includes a slot 78 that connects the guide wire channel 60 to the exterior of the shaft for allowing a guide wire to radially exit the guide wire channel 60. The slot 78 extends from the shaft opening 76 to a position distally thereof, such as the beginning of the optional taper or catheter distal section. As best shown in the embodiment of FIG. 3, the slot 78 is formed in the core body 80 and the optional outer sleeve 82 of the catheter shaft 36. In embodiments that do not include an outer sleeve, the slot 78 is formed in the core body. As such, the slot 78 and the guide wire channel 60 together define a slotted channel section. The slotted channel section may define, for example, a general U or C-shaped channel, although other slotted configurations may be practiced with the present invention, and are contemplated to be within the scope of the present invention, as claimed.

Figure 15:
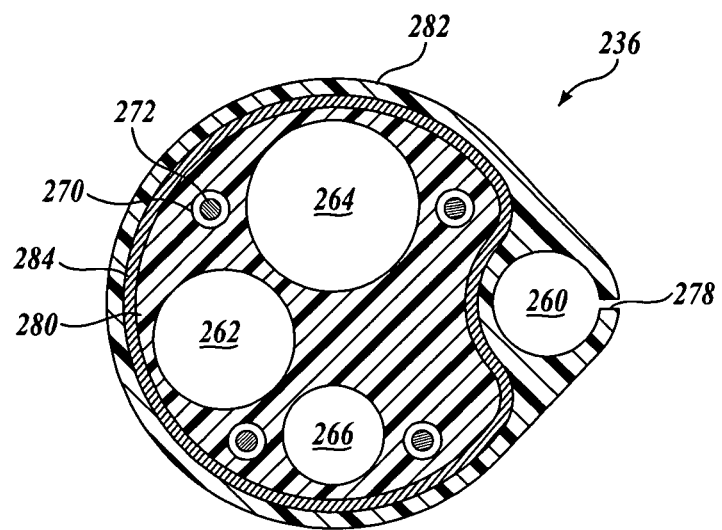
FIG. 15 is a cross-sectional view taken along line 15-15 in FIG. 14.

In use, the slotted channel section serves to contain, but not constrain, a guide wire as it is routed between the opening 76 and the beginning of the distal section 44. The guide wire channel 60 is sufficiently large to allow unhindered radial guide wire movement therein. In the embodiment of FIG. 3, the slot 78 is sized to allow passage of a conventional guide wire (e.g., 0.025 inch-0.035 inch diameter guide wires) radially therethrough. In several embodiments, the slot 78 is substantially equal to or slightly larger than the diameter of the guide wire channel 60. In other embodiments, the slot 78 may be smaller than the diameter of the guide wire channel 60, as shown, for example, in FIG. 3. In yet other embodiments, the slot may be smaller than the diameter of the guide wire routed therethrough, as shown in the example of FIG. 15. In these embodiments, the slotted channel section is configured to allow separation at the opening to the guide wire channel to promote radial passage of the guide wire.

Figure 18A:
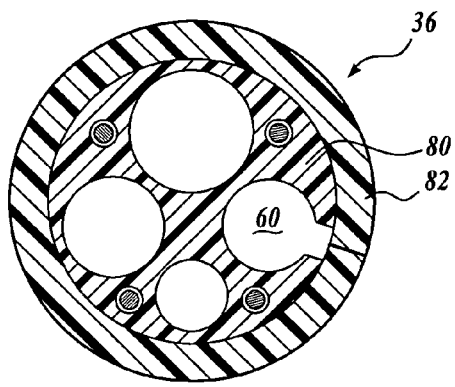
FIGS. 18A-18D are cross-sectional views of exemplary embodiments of the catheter.
Figure 18B:
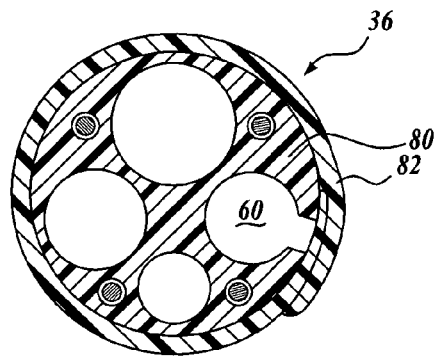
Figure 18C:
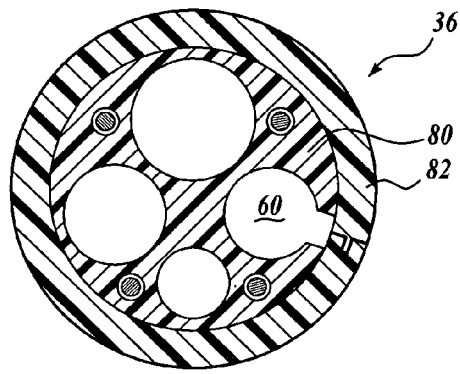
Figure 18D:
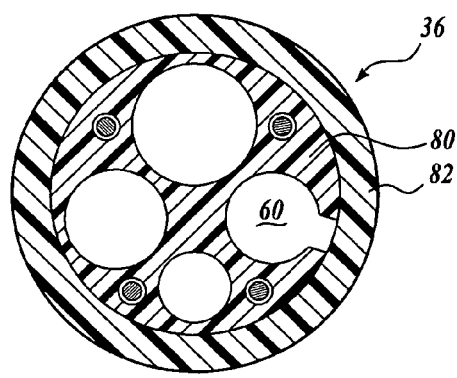

While the embodiments shown in FIGS. 3, 5, and 6 employ a slotted configuration for allowing a guide wire to radially exit the guide wire channel 60, other configurations are contemplated to be within the scope of the present invention, as claimed. For example, instead of a portion of the slot 78 being formed in the outer sleeve 82, the outer sleeve 82 may be formed with a slit with abutting edges, a flap with overlapping edges or interlocking edges, as shown in FIGS. 18A-18C, respectively. Alternatively, as shown in FIG. 18D, a layer of material of the outer sleeve disposed in-between the guide wire channel 60 and the exterior of the shaft may be relatively thin, weakened to promote tearing, perforated, or is composed of a generally soft material for providing a weak wall through which a guide wire can be pulled.

Figure 19A:
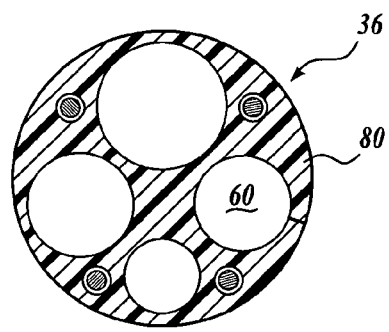
FIGS. 19A-19D are cross-sectional views of additional exemplary embodiments of the catheter.
Figure 19B:
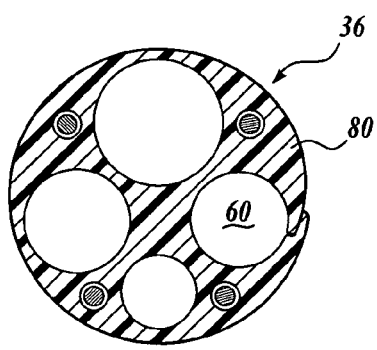
Figure 19C:
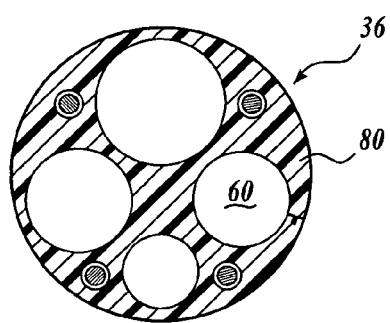
Figure 19D:
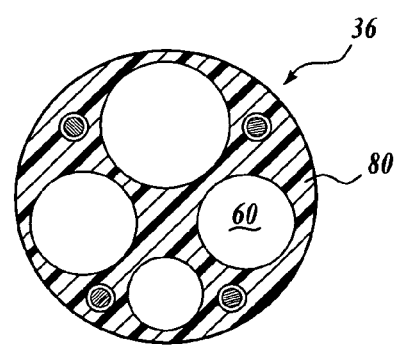

FIGS. 19A-19D illustrate other exemplary configurations for allowing a guide wire to radially exit the guide wire channel 60. In these examples, the outer sleeve has been omitted. As best shown in FIGS. 19A-19C, the catheter shaft 36 may be formed with a slit with abutting edges, a flap with overlapping edges or interlocking edges, respectively. Alternatively, as shown in FIG. 19D, a layer of material disposed in-between the guide wire channel 60 and the exterior of the shaft may be relatively thin, weakened to promote tearing, perforated, or is a generally soft material for providing a weak wall through which a guide wire can be pulled. In this regard, these aforementioned sections, along with the slotted channel section described above, may be referred herein as rapid exchange channel sections of the catheter shaft.

Returning to FIG. 1, the catheter assembly 20 may further include a guide wire port 26 positioned, for example, along a portion of the proximal section 40 of the catheter shaft 36. In use, the guide wire port 26 communicates with the shaft opening 76 (see FIGS. 5 and 6) for providing access to the guide wire channel. As such, the guide wire port 26 may be positioned proximate or near the proximal end 30 of the catheter 24 or may be disposed further distally of the proximal end 30 along the catheter 24 toward the optional taper 48, depending on the location of the shaft opening. Although it should be recognized that the guide wire port 26 may be located at any location distally of the proximal end 30 of the catheter 24, in one embodiment it is located approximately between 140 and 180 centimeters from the taper 48.

Referring now to FIGS. 5 and 6, one exemplary embodiment of the guide wire port 26 is shown in more detail. As best shown in the embodiments of FIGS. 5 and 6, the guide wire port 26 may include a main body 86 and a funnel-shaped extension 88. The funnel-shaped extension 88 is connected to and disposed adjacent the main body 86. The main body 86 includes a main channel 90 extending therethrough. The main channel 90 is sized to accommodate the catheter shaft 36 in a slidably restricting manner. Once positioned on the catheter shaft 36 in a suitable position, the guide wire port 26 is fixedly secured to the catheter shaft 36.

In the embodiment shown in FIGS. 5 and 6, the funnel-shaped extension 88 includes a funnel channel 92 having a proximal opening 94 and a distal opening 96. In several embodiments, the proximal opening 94 of the funnel channel 92 may be dimensioned significantly larger than the guide wire to be used with the catheter so that the guide wire may be easily inserted into the funnel channel 92. The distal opening 96 of the funnel channel 92 is positioned and sized to communicate with the guide wire channel 60 of the catheter shaft 36, as will be described in more detail below, so that the guide wire may be inserted into the funnel channel 92 through the proximal opening 94 and into the guide wire channel 60 through the distal opening 96. The distal end of the main body 86 and the distal portion of the funnel-shaped extension 88 converge together to define a merged section 100. The main channel 90 and the funnel channel 92 also merge together into a merged channel 102 in the merged section 100. The funnel-shaped extension 88 further includes a slot or slit 104 for providing access to the funnel channel 92. The slot 104 extends along the length of the funnel-shaped extension 88 and the distal merged section 100. The slot 104 is sized to allow passage of a conventional guide wire therethrough.

When assembled, the slot 104 of the guide wire port 26 is substantially aligned with the slot 78, the slit, or other means for allowing a guide wire to radially exit the guide wire channel 60, as shown in the embodiment of FIGS. 5 and 6. Additionally, the shaft opening 76 is aligned with and is dimensioned to correspond to the distal opening 96 of the tunnel channel 92 for communication therebetween. As such, the rapid exchange channel section and the guide wire port 26 allows rapid exchange of either the guide wire or of the catheter 24 when an alternative catheter or guide wire is desired during certain medical procedures. Additionally, shorter length guide wires, such as 260 centimeter guide wires, may be used since the guide wire does not need to pass though the proximal end of the catheter shaft 36. Alternatively, it will be appreciated that such a catheter shaft construction as shown and described herein also allows for longer length guide wires, such as the conventional 450 centimeter guide wires, to be routed from the proximal end 30 of the catheter shaft 36 to the distal end 32 of the catheter shaft 36, and beyond.

In exemplary embodiments of the present invention, the catheter shaft 36 may have one or more of the following dimensions. For example, the proximal section 40 may be approximately 200-240 centimeters in length and have an outside diameter of approximately 12 French. In this embodiment, the outer diameter of the core body 80 is approximately 0.125 inches. The core body 80 may house a working channel 60 having a diameter of approximately 0.054 inches, an optical channel 62 having a diameter of approximately 0.044 inches, an irrigation channel 66 having a diameter of approximately 0.032 inches, a guide wire channel 64 having a diameter of approximately 0.040 inches (for use with a 0.035 inch diameter guide wire), and four steering wire channels 70 each having a diameter of approximately 0.012 inches. The core body 80 may be sheathed with an outer sleeve 82 having a thickness of approximately 0.006-0.012 inches. Alternatively, the core body can remain unsheathed and have an outer diameter of approximately 11-12 French. It will be appreciated that the aforementioned dimensions may have tolerances of approximately 0.002 inches.

The distal section 44 may be approximately 10-40 centimeters in length and have an outside diameter of approximately 11 French. In this embodiment, the outer diameter of the core body 80 is approximately 0.125 inches. The dimensions of the aforementioned channels are substantially identical. The core body 80 may be sheathed with a reinforcement layer 84 and an outer sleeve 82. The reinforcement layer 84 has a thickness of approximately 0.0035 inches and the outer sleeve 82 has a thickness of approximately 0.006 inches. Alternatively, the distal section of the core body can omit the reinforcement layer and outer sleeve, and have an outer diameter of approximately 10-11 French. It will be appreciated that the aforementioned dimensions may have tolerances of approximately 0.002 inches.

In other embodiments, such as those illustrated in FIGS. 7-9, the outside diameter of the proximal section core body 80 may be approximately 0.145 inches or around 11 French. The core body 80 of the proximal section 40 in this embodiment may also be encased with an outer sleeve 82 of approximately 0.006 inch thickness, resulting in an outer diameter of the shaft of approximately 12 French. In this embodiment, the outer diameter of the core body 80 of the distal section 44 is approximately 0.125 inches, and may include a reinforcement layer (not shown) of approximately 0.0035 inch thickness and/or an outer sleeve 82 of approximately 0.006 inch thickness. Alternatively, the proximal section of the core body can remain unsheathed and have an outer diameter of approximately 12 French, and the distal section of the core body can remain unsheathed and unreinforced and have an outer diameter of approximately 11 French.

In yet other embodiments, the catheter may be used with an 0.025 inch diameter guide wire. As such, the diameters of the internal channels may be adjusted so that the overall outer diameter of the catheter is reduced. For example, in this embodiment, the outer diameter of the core body 80 may be approximately 0.115 inches. The core body 80 may house a working channel 60 having a diameter of approximately 0.054 inches, an optical channel 62 having a diameter of approximately 0.040 inches, an irrigation channel 66 having a diameter of approximately 0.030 inches, a guide wire channel 64 having a diameter of approximately 0.030 inches, and four steering wire channels 70 each having a diameter of approximately 0.012 inches. The core body 80 may be sheathed with an outer sleeve 82 having a thickness of approximately 0.050 inches. Accordingly, the outside diameter of the catheter is approximately 0.125 inches, or slightly less than 10 French. It will be appreciated that the aforementioned dimensions may have tolerances of approximately 0.002 inches. It will further be appreciated that in this embodiment, the outer sleeve 82 may have a thickness of approximately 0.010-0.012 inches on the proximal section to increase stiffness, etc, resulting in a proximal section having an outer diameter of approximately 11 French.

Returning to the embodiment of FIG. 1, the catheter 24 may be functionally connected to the catheter handle 22. FIG. 1 illustrates one exemplary embodiment of a catheter handle that may be practiced with embodiments of the catheter 24, although many others may be alternatively used. As best shown in FIG. 1, the handle 22 includes a handle housing 106 to which a steering mechanism 108, one or more ports, and an optional endoscope attachment device (not shown) is operatively connected. The one or more ports may include any combination of a working channel port 112 for providing access to the working channel from the proximal end of the catheter 24, an optical channel port 114 for providing access to the optical channel from the proximal end of the catheter 24, and a fluid channel port 116 for providing access to the irrigation/insufflation channel from the proximal end of the catheter 24. The catheter handle 22 may include an optional guide wire port 118 for providing access to the guide wire channel from the proximal end of the catheter 24.

While the ports 112, 114, and 116 are shown on the handle 22, it will be appreciated that ports for accessing the one or more channels of the catheter shaft may additionally or alternatively be disposed anywhere along the catheter shaft, preferably somewhere along the proximal section.

The steering mechanism 108 of the catheter handle 22 controls deflection of the distal end 32 of the catheter 24. The steering mechanism 108 may be any known or future developed mechanism that is capable of deflecting the distal end of the catheter by selectively pulling the steering wires. In the embodiment shown in FIG. 1, the steering mechanism 108 includes two rotatable knobs for effecting 4-way steering of the catheter distal end in the up/down direction and in the right/left direction. This mechanism 108 includes an outer knob 110A to control up/down steering and an inner knob 110B to control right/left steering. Alternatively, the inner knob 110B may function to control right/left steering and an outer knob 110A may function to control up/down steering. The knobs interface with the distal end 32 of the catheter 30 via the steering wires 72 (See FIG. 4) that extend through the catheter 24.

While a manually actuated steering mechanism for effecting 4-way steering of the distal is shown, it will be appreciated that a manually actuated steering mechanism that effects 2-way steering may be practiced with and is therefore considered to be within the scope of the present invention. Please see co-pending U.S. application Ser. No. 11/089,520, which is hereby incorporated by reference, for a more detailed description of steering mechanisms that may be practiced with the present invention. In embodiments of the catheter handle that connect to non-steerable catheters, it will be appreciated that the steering mechanism may be omitted from the handle.

In use, various treatment or diagnostic devices, such as stone retrieval baskets, lasers, biopsy forceps, etc. may be inserted into the working channel port 112 of the catheter handle 22 and routed to the treatment area located distally of the catheter distal end. Optical devices, such as vision catheters or fiberscopes, may be inserted into the optical channel port 114 of the catheter handle 22 and routed to the treatment area located distally of the catheter distal end. Fluids, such as liquids or gases, may be injected into the fluid port 116 and delivered to the distal end of the catheter. Finally, a guide wire may be inserted into the optional guide wire port or working channel port if desired, and routed to the treatment area located distally of the catheter distal end.

For examples of imaging devices that may be practiced with embodiments of the present invention, please see the description of the fiber optic cable in co-pending U.S. application Ser. No. 10/914,411, filed Aug. 9, 2004, the fiberscope and methods of use in co-pending U.S. application Ser. No. 11/089,520, and the guide wire scope described in U.S. Published Patent Application Number 2004/0034311 A1, the disclosures of which are hereby incorporated by reference.

Figure 10:
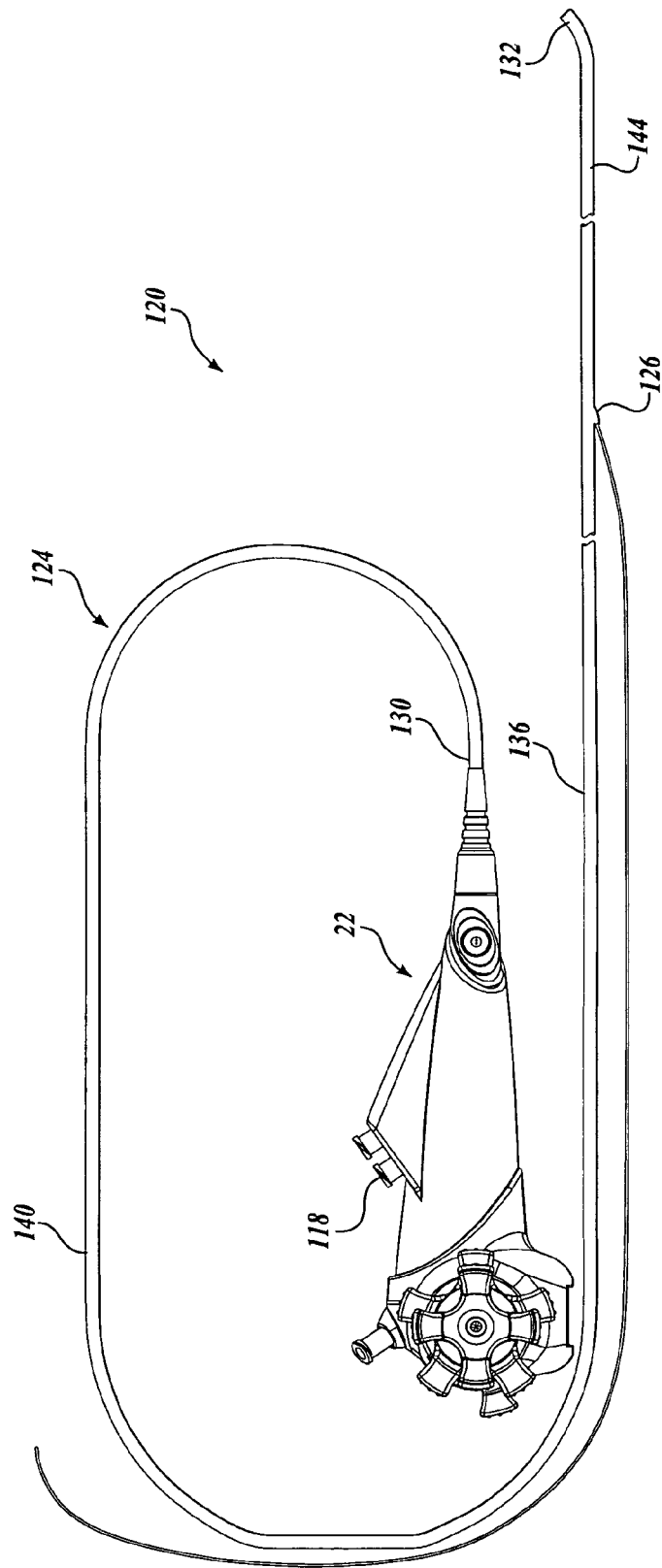
FIG. 10 is a plan view of another exemplary embodiment of a catheter assembly formed in accordance with aspects of the present invention.

Turning now to FIGS. 10-13, there is shown another representative embodiment of a catheter assembly, generally designated 120. The catheter assembly 120 is substantially identical in construction, materials, and operation as the catheter assembly 20, except for the differences that will now be described. As best shown in FIG. 10, the catheter assembly 120 may include a catheter handle 22, a catheter 124, and a guide wire port 126 position along a portion of the catheter 124. The catheter 124 includes a proximal end 130 that may be operatively connected to the catheter handle 22 and a distal end 132 that may be inserted into, for example, a working channel of an endoscope or a passageway of a patient.

The catheter 124 includes a shaft 136 having a generally cylindrically-shaped body of substantially uniform diameter. The shaft 136 comprises a proximal section 140 and a distal section 144. In several embodiments, the distal section 144 or portions thereof may be constructed to be more flexible or bendable so that the distal end 132 of the catheter shaft 136 may be steered in one or more directions during use.

Turning now to FIG. 11, there is shown an end view of the catheter shaft 136 positioned within a working channel WC of an endoscope. Substantially similar to the catheter shaft 36 of FIGS. 2-4, the catheter shaft 136 may define an optical channel 162 and a working channel 164 that extend the length of the catheter from its proximal end 130 to its distal end 132. The shaft 136 also includes a dedicated guide wire channel 160 that extends the entire length of the catheter 124 through which a guide wire can be routed to and from the treatment area. However, in contrast to the catheter shaft 36 shown in FIG. 3 and described above, the rapid exchange section of the catheter shaft 36 is omitted. The shaft 136 may further include an additional channel 166 that extends the entire length of the catheter shaft 136 for use as an irrigation/insufflations channel or fluid delivery channel.

In one embodiment, the catheter shaft may be constructed of a core body 180, an outer sleeve 182, and an inner reinforcement sheath 184. The inner reinforcement sheath 184 is disposed in-between the core body 180 and the outer sleeve 182, as best shown in FIG. 12, and functions to provide increased column strength and torsional rigidity. The inner reinforcement sheath 184 and outer sleeve 182 extend along the catheter shaft 136 from the proximal end 130 to the distal end 132, or portions thereof.

Figure 13:
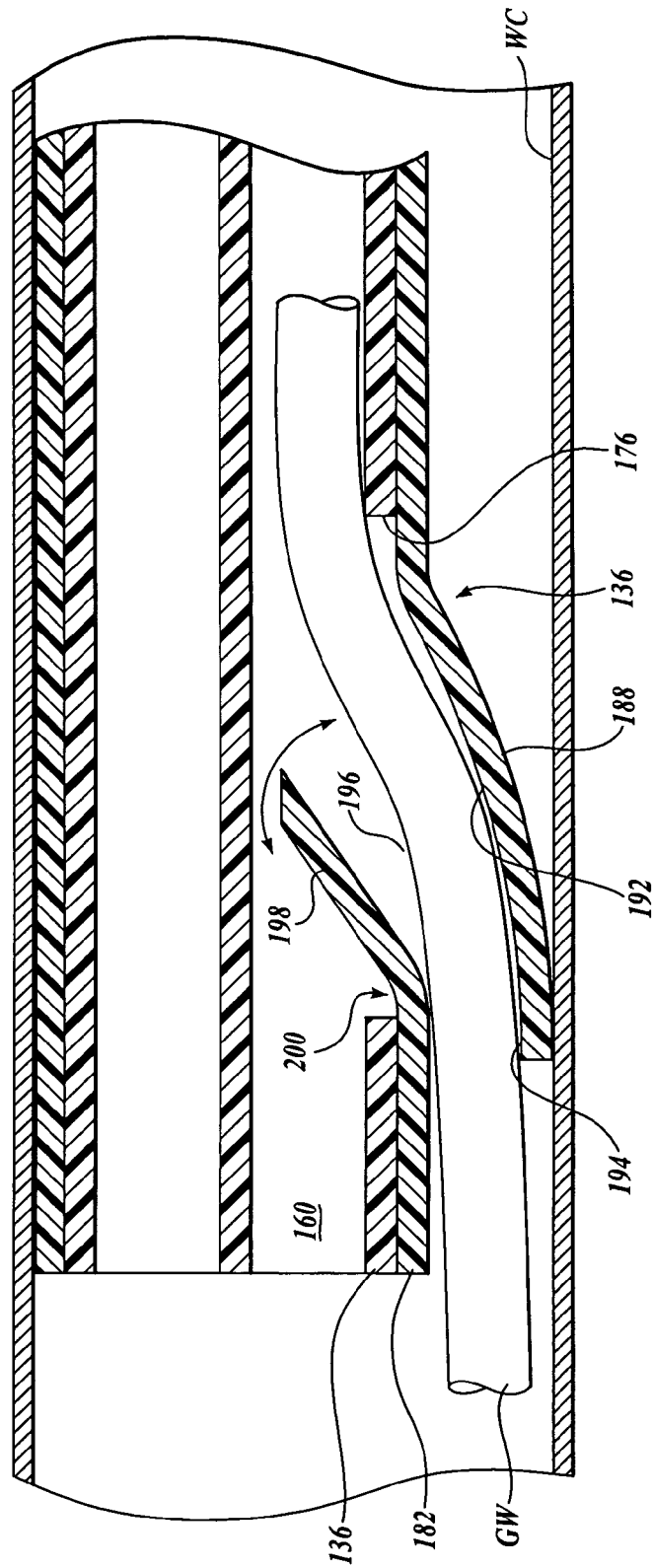
FIG. 13 is a partial side cross-sectional view of one exemplary embodiment of a guide wire port formed in accordance with aspects of the present invention.
Figure 14:
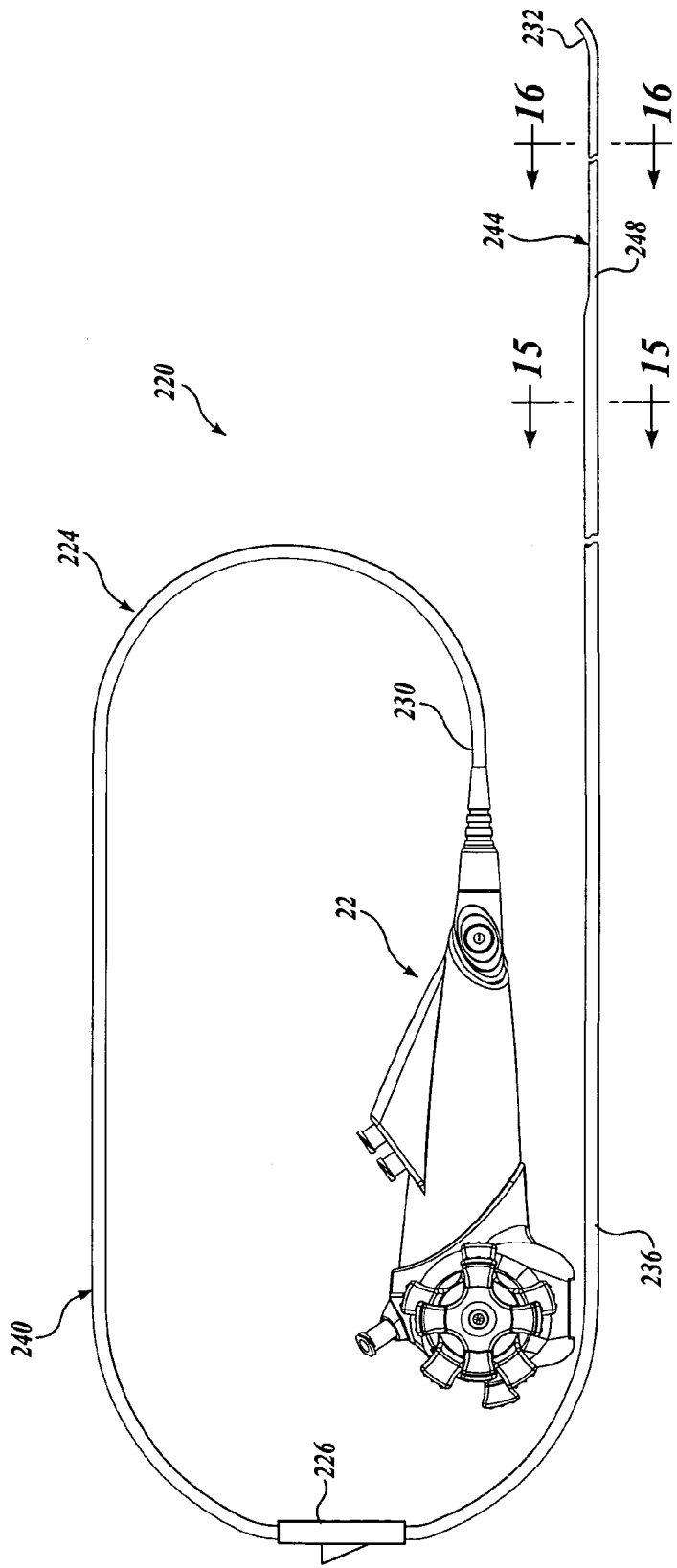
FIG. 14 is a plan view of another exemplary embodiment of a catheter assembly formed in accordance with aspects of the present invention.

Finally, the catheter shaft may include an opening 176 formed along a portion of the outer surface of the shaft and positioned, for example, near or at the beginning of the distal section, as best shown in FIG. 13. The opening 176 is formed so as to communicate with and provide access to the guide wire channel 164 from a position that is external to the shaft. As such, the opening 176 in the embodiment shown is formed through the outer sleeve 182, the reinforcement sheath 184 (not shown in FIG. 13 for ease of illustration), and a portion of the core body 180. As will be described in detail below, the opening 176 communicates with the guide wire port 126 for facilitating the insertion of a guide wire into the guide wire channel during use.

Returning to FIG. 10, the catheter 124 further includes a guide wire port 126 positioned near or at the beginning of the distal section 144 for providing access to a guide wire channel of the catheter shaft 136. In one embodiment, the guide wire port is located approximately between 5 and 30 centimeters from the distal end of the catheter shaft. In that regard, shorter guide wires, such as those approximately 260 cm to 450 cm, may be employed by the catheter 124. Referring now to FIG. 13, the guide wire port 126 is shown in more detail. As best shown in FIG. 13, the guide wire port 126 includes an extension section 188 and an optional deflector 198. The extension section 180 is disposed adjacent the catheter shaft 136. In several embodiments of the present invention, the guide wire port 126 can be constructed as a section of the outer sleeve 182.

The extension 188 includes a channel 192 having a proximal opening 194 and a distal opening 196. The proximal opening 194 of the channel 192 is preferably larger than the distal opening 196 to form a somewhat funnel-like channel. It will be appreciated that the proximal opening 194 of the guide wire port 126 is constructed as large as possible so that the guide wire GW may be easily inserted into the channel while also allowing the catheter shaft 136 to be inserted into a standard 4.2 mm inside diameter endoscope working channel WC as best shown in FIG. 11. The distal opening 196 of the channel 192 is positioned and sized to communicate with the shaft opening 176, and in turn, the guide wire channel 164 of the catheter shaft 136 so that the guide wire GW may be inserted into the guide wire channel 164 through the distal opening 196 and shaft opening 176.

The guide wire port 126 may be further formed with an optional deflector 198. In one embodiment, the deflector 198 is positioned to inwardly extend into the shaft opening 176 and a substantial portion of the guide wire channel 160. The deflector 198 is operable to pivot about area 200 so as to either be capable of blocking access to the guide wire channel 164 of the catheter shaft 136 or the guide wire port channel 192. In several embodiments, the deflector 198 is inwardly biased to the position shown in FIG. 13. In this position, a guide wire may be front loaded into either the optional guide wire port 118 on the catheter handle 22 (see FIG. 10) and routed through the catheter shaft to the distal end of the catheter or inserted into the guide wire port proximal opening 194 and routed to the distal end of the catheter. It will be appreciated that in this embodiment, if routed down the guide wire port on the handle, the guide wire would temporarily displace the deflector so that the guide wire could pass through.

Once the guide wire is removed, the deflector 198 is again biased to the position in FIG. 13. In this manner, the catheter is also back loadable. For example, when the catheter is routed over a guide wire previously placed within a body channel, the guide wire enters the distal end opening 196 of the guide wire channel 192 and then is routed through the guide wire port channel 192 as a result of the deflector 198. It will also be appreciated that the deflector 198 could be biased in a position that blocks the distal opening 196 of the guide wire port channel 192 so that the back loadable guide wire is routed through the guide wire channel 160 to the catheter's proximal end and out of the optional guide wire port of the catheter handle.

In exemplary embodiments of the present invention, the catheter 124 may have one or more of the following dimensions. For example, the proximal section 140 may be approximately 200-240 centimeters in length and have an outside diameter of approximately 10 French. The distal section 144 may be approximately 10-40 centimeters in length and have an outside diameter of approximately 10 French. In this embodiment, the outer diameter of the core body 180 is approximately 0.118 inches. The core body 180 may house a working channel 160 having a diameter of approximately 0.050 inches, an optical channel 162 having a diameter of approximately 0.042 inches, an irrigation channel 166 having a diameter of approximately 0.030 inches, a guide wire channel 164 having a diameter of approximately 0.040 inches (for use with a 0.035 inch diameter guide wire), and four steering wire channels 170 each having a diameter of approximately 0.012 inches. The core body 180 may be sheathed with a reinforcement layer 184 and an outer sleeve 182. For example, a reinforcement layer 184 may be employed having a thickness of approximately 0.0035 inches and the outer sleeve 182 may be employed having a thickness of approximately 0.0035 inches. It will be appreciated that the aforementioned dimensions may have tolerances of approximately 0.002 inches.

Turning now to FIGS. 14-17, there is shown another representative embodiment of a catheter assembly, generally designated 220. The catheter assembly 220 is substantially identical in construction, materials, and operation as the catheter assembly 20, except for the differences that will now be described. The catheter assembly 220 may include a catheter handle 22, a catheter 224, and a guide wire port 226 positioned along a portion of the proximal section of catheter 224. The catheter 224 includes a proximal end 230 that may be operatively connected to the catheter handle 22 and a distal end 232 that may be inserted into, for example, a working channel of an endoscope or a passageway of a patient. The catheter 224 includes a shaft 236 comprising a proximal section 240, a distal section 244, and a taper 248, which acts as a transition between the proximal section 240 and the distal section 244 of the catheter 224. In several embodiments, the distal section 244 or portions thereof may be constructed to be more flexible or bendable so that the distal end 232 of the catheter shaft 236 may be steered in one or more directions during use.

Figure 16:
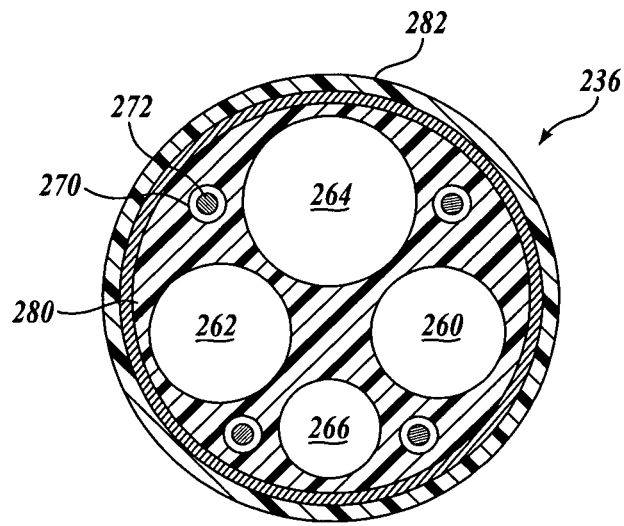
FIG. 16 is a cross-sectional view taken along line 16-16 in FIG. 14.

Turning now to FIGS. 15 and 16, there are shown cross-sectional views of the proximal section 240 taken distally of the guide wire port 126 and the distal section 144, respectively. Substantially similar to the catheter shaft 36 of FIG. 3, the catheter shaft 236 may include an optical channel 262 and a working channel 264 that extend the length of the catheter or portions thereof. The shaft 236 may also include an additional channel 266 for use as an irrigation/insufflations channel or fluid delivery channel. The shaft 236 further includes a dedicated guide wire channel 260 that extends the entire length of the catheter through which a guide wire can be routed to and from the treatment area. The guide wire channel 260 includes a slot 278 from the guide wire port 226 to the beginning of the taper of the catheter shaft 236 as shown in FIG. 16. As described in more detail above, other means for accessing the guide wire channel may be employed, including those shown in FIGS. 18 and 19.

As best shown in FIGS. 15 and 16, the shaft may be constructed of a core body 280, an outer sleeve 382, and an inner reinforcement sheath 284 disposed in-between the core body 280 and the outer sleeve 282 for providing improved column strength and torsional rigidity. The inner reinforcement sheath 284 and outer sleeve 282 extend along the catheter shaft from the proximal end to the distal end, or portions thereof. The outer sleeve 282 in this embodiment forms the slotted channel section as it extends from the guide wire port 226 to the taper 248. At the taper 248, the slot 278 of the guide wire channel 260 terminates and the guide wire channel 260 merges gradually into the core body 280 of the catheter shaft, as best shown in FIG. 17. It will be appreciated that in this portion of the catheter shaft, the reinforcement sheath 284 is omitted or an aperture is created so that the guide wire channel 260 can transition from being disposed outside of the core body 280, as best shown in FIG. 15, to being disposed inside the core body 280, as shown best in FIG. 16.

In exemplary embodiments of the present invention, the catheter 224 may have one or more of the following dimensions. For example, the proximal section 240 may be approximately 200-240 centimeters in length and have an outside width of approximately 0.147-0.155 inches and a height of approximately 0.132-0.135. The distal section 244 may be approximately 10-40 centimeters in length and have an outside diameter of approximately 10-11 French. The core body 280 may house a working channel 260 having a diameter of approximately 0.054 inches, an optical channel 262 having a diameter of approximately 0.044 inches, an irrigation channel 166 having a diameter of approximately 0.030 inches, a guide wire channel 164 having a diameter of approximately 0.030-0.040 inches (depending on use of a 0.025 or 0.035 inch diameter guide wire), and four steering wire channels 170 each having a diameter of approximately 0.012 inches. The core body 180 may be sheathed with a reinforcement layer 184 and an outer sleeve 182. In these embodiments, the reinforcement layer 284 has a thickness of approximately 0.0035 inches and the outer sleeve 282 has a thickness of approximately 0.0035 inches. It will be appreciated that the aforementioned dimensions may have tolerances of approximately 0.002 inches.

The principles, representative embodiments, and modes of operation of the present invention have been described in the foregoing description. However, aspects of the present invention which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present invention. Accordingly, it is expressly intended that all such variations, changes, and equivalents fall within the spirit and scope of the present invention, as claimed.

The embodiments of the invention in which an exclusive property or privilege is claimed are defined as follows:

1. A catheter, comprising:
   an elongated shaft having a proximal end and a distal end;
   a guide wire channel extending along at least a portion of the shaft in-between the proximal and distal ends;
   at least one channel disposed within the shaft and extending to the distal end;
   a guide wire opening disposed in communication with the guide wire channel of the shaft such that a guide wire may be insertable into the guide wire opening and routed into the guide wire channel; and
   wherein the shaft is configured for providing radial access from a position exteriorly of the shaft to a portion of the guide wire channel that extends between the guide wire opening and a position proximal the distal end of the shaft in order to allow a guide wire to radially exit the shaft, wherein the shaft includes a core body and an outer sleeve permanently attached to the core body by engagement between an outer surface of the core body and an inner surface of the outer sleeve, a discontinuity in the outer sleeve providing the radial access to the guide wire channel.

2. The catheter of claim 1, further comprising at least one steering wire for deflecting the distal end of the shaft.

3. The catheter of claim 1, wherein the discontinuity includes a slot for allowing the guide wire to radially exit the shaft, the slot and guide wire channel define a slotted channel section, and the slot includes substantially parallel edges separated by a gap.

4. The catheter of claim 3, wherein the slotted channel section terminates as the guide wire channel transitions from being disposed outside of the core body to being disposed inside of the core body.

5. The catheter of claim 1, wherein the shaft includes a proximal section and a distal section, and wherein the diameter of the core body along a portion of the proximal section is greater than the diameter of the core body along a portion of the distal section.

6. The catheter of claim 1, wherein the shaft includes a proximal section and a distal section, and wherein the outer sleeve along the proximal section is thicker than the outer sleeve along the distal section.

7. The catheter of claim 1, further comprising an intermediate sleeve disposed radially between the core body and the outer sleeve at a distal portion of the shaft, a proximal end of the intermediate sleeve terminating distally of a proximal end of the discontinuity.

8. The catheter of claim 1, further comprising a guide wire port fixedly secured to a proximal portion of the shaft, wherein the guide wire port includes a funnel shaped extension including a port opening proximal to the guide wire opening.

9. The catheter of claim 8, wherein the discontinuity includes a first slot extending from the guide wire opening to a distal section of the shaft, and wherein the funnel-shaped extension includes a port channel in communication with the port opening and the guide wire opening.

10. The catheter of claim 9, wherein the funnel-shaped extension includes a second slot defined on an exterior surface of the funnel-shaped extension and extending from the first slot of the shaft to the port opening of the funnel-shaped extension.

11. The catheter of claim 1, wherein a diameter of the outer sleeve tapers between a proximal section of the shaft and a distal section of the shaft, and the discontinuity in the outer sleeve terminates at the taper.

12. The catheter of claim 1, wherein the discontinuity includes a slit through the outer sleeve, the slit including a distal end terminating proximally of a distal end of the outer sleeve.

13. The catheter of claim 1, wherein the discontinuity includes an opening through the outer sleeve, the opening including a distal end terminating proximally of a distal end of the outer sleeve.

14. The catheter of claim 13, wherein the opening extends through at least a portion of the core body and into the guidewire channel.

15. The catheter of claim 1, wherein the engagement between the outer surface of the core body and the inner surface of the outer sleeve is provided by at least one of laminating the outer sleeve over the core body, co-extruding the outer sleeve and the core body, heat shrinking the outer sleeve over the core body, and adhesively bonding the outer sleeve to the core body.

16. The catheter of claim 1, wherein the outer sleeve extends from a proximalmost end of the shaft to a distalmost end of the shaft.

17. A medical device, comprising:
 an elongated shaft including a proximal end and a distal end;
 a channel for receiving an instrument, wherein the channel extends along at least a portion of the shaft between the proximal and distal ends;
 a channel opening disposed on a side surface of the shaft and in communication with the channel;
 a slot disposed on the side surface of the shaft and configured to provide access to the channel, wherein the slot includes a proximal end, and the slot extends between the channel opening and a position proximal the distal end of the shaft; and
 wherein the shaft includes a core body extending between the proximal end and the distal end of the shaft, an outer sleeve covering the core body, and an intermediate sleeve disposed radially between the outer sleeve and the core body and extending between only the distal end of the shaft and the position proximal the distal end of shaft, the intermediate sleeve including a proximal end terminating distally of the proximal end of the slot, and the slot extending through the outer sleeve.

18. The medical device of claim 17, wherein the intermediate sleeve is permanently attached to the core body, and the outer sleeve is permanently attached to the intermediate sleeve and the core body, the outer sleeve being configured to lock the intermediate sleeve in place and secure the intermediate sleeve to the core body.

19. The medical device of claim 18, wherein the slot extends through a portion of the core body into the channel.

20. The medical device of claim 17, wherein a diameter of the outer sleeve tapers between a proximal section of the shaft and a distal section of the shaft, and the slot terminates at the taper.

21. The medical device of claim 17, wherein a gap in the outer sleeve forms at least a portion of the slot, and the slot includes a distal end terminating proximally of a distal end of the outer sleeve.

22. The medical device of claim 17, wherein the outer sleeve extends from a proximalmost end of the core body to the distalmost end of the core body.

23. A medical device, comprising:
 an elongated shaft including:
  a channel for receiving an instrument, wherein the channel extends along at least a portion of the shaft between a proximal end and a distal end of the shaft;
  a channel opening disposed on a side surface of the shaft and in communication with the channel;
  a first slot disposed on the side surface of the shaft and configured to provide access to the channel, wherein the first slot includes a proximal end, and the first slot extends between the channel opening and a position proximal the distal end of the shaft;
  a core body extending between the proximal end and the distal end of the shaft;
  an outer sleeve covering the core body, the first slot extending through the outer sleeve and into the channel;
  an intermediate sleeve disposed radially between the outer sleeve and the core body and extending between only the distal end of the shaft and the position proximal the distal end of shaft, the intermediate sleeve including a proximal end terminating distally of the proximal end of the first slot, wherein the intermediate sleeve is permanently attached to the core body, and the outer sleeve is permanently attached to the intermediate sleeve and the core body; and
  at least one control member extending along the shaft and configured to deflect the distal end of the shaft;
 a port fixedly secured to a proximal portion of the shaft, wherein the port includes a funnel-shaped extension including a port opening proximal to the channel opening, a port channel in communication with the port opening and the channel opening, and a second slot defined on an exterior surface of the funnel-shaped extension and extending from the first slot of the shaft to the port opening of the funnel-shaped extension; and
 a handle coupled to the shaft and including a steering mechanism operably coupled to the at least one control member, wherein actuation of the steering mechanism is configured to deflect the distal end of the shaft.

24. The medical device of claim 23, wherein the first slot includes a break in the outer sleeve.

25. The medical device of claim 23, wherein the outer sleeve is configured to lock the intermediate sleeve in place and secure the intermediate sleeve to the core body.

* * * * *